(12) United States Patent
Fehre et al.

(10) Patent No.: US 7,428,295 B2
(45) Date of Patent: Sep. 23, 2008

(54) METHOD AND X-RAY APPARATUS FOR EXPOSURE OF A PATIENT AT VARIABLE DISTANCES RELATIVE TO AN X-RAY SOURCE

(75) Inventors: Jens Fehre, Hausen (DE); Rainer Kaltschmidt, Eckental/Brand (DE); Markus Ludwig, Wolfen (DE); Ulrich Will, Kunreuth (DE)

(73) Assignee: Siemens Aktiengesellschaft, Munich (DE)

( * ) Notice: Subject to any disclaimer, the term of this patent is extended or adjusted under 35 U.S.C. 154(b) by 111 days.

(21) Appl. No.: 11/418,424

(22) Filed: May 4, 2006

(65) Prior Publication Data

US 2006/0269044 A1    Nov. 30, 2006

(30) Foreign Application Priority Data

May 4, 2005    (DE) .................. 10 2005 020 898

(51) Int. Cl.
*H05G 1/42* (2006.01)
*H05G 1/44* (2006.01)

(52) U.S. Cl. .................. 378/108; 378/97; 378/98.7

(58) Field of Classification Search ............ 378/97, 378/98.7, 108
See application file for complete search history.

(56) References Cited

U.S. PATENT DOCUMENTS

| 4,590,603 | A  | * | 5/1986  | Relihan et al. ............. 378/108 |
| 4,896,343 | A  | * | 1/1990  | Saunders .................... 378/95 |
| 6,977,989 | B2 | * | 12/2005 | Bothe et al. ................ 378/108 |
| 7,054,412 | B2 | * | 5/2006  | Scheuering ................. 378/108 |
| 7,194,065 | B1 | * | 3/2007  | Boutenko et al. ........... 378/108 |
| 2007/0140429 | A1 | * | 6/2007 | Hoheisel ..................... 378/117 |

FOREIGN PATENT DOCUMENTS

| DE | 20 10 360 C3 |   | 4/1983 |
| DE | 10118183 A1  | * | 11/2002 |

* cited by examiner

*Primary Examiner*—Edward J. Glick
*Assistant Examiner*—Thomas R Artman
(74) *Attorney, Agent, or Firm*—Schiff Hardin LLP

(57) ABSTRACT

In a method and x-ray apparatus for exposure of a patient who can be placed at a variable distance relative to an x-ray source, the dose rate emitted by the x-ray source is reduced given reduction of the distance and/or increased given increase of the distance.

14 Claims, 3 Drawing Sheets

METHOD AND X-RAY APPARATUS FOR EXPOSURE OF A PATIENT AT VARIABLE DISTANCES RELATIVE TO AN X-RAY SOURCE

BACKGROUND OF THE INVENTION

1. Field of the Invention

The present invention concerns a method and an x-ray apparatus for radiation exposure of a patient who can be placed at a variable distance relative to an x-ray source.

2. Description of the Prior Art

X-ray methods and x-ray apparatuses have been used for many decades for medical imaging, in which x-rays are directed through the body of a patient in the form of a living person or animal. Despite this large usage in medicine, such ionizing radiation is not free of health risks for the patient. The use of x-ray radiation on living patients is therefore heavily legally regulated. In particular, maximal allowable limit values exist for the dose rate of x-ray radiation on the body surface of a patient. 21 C.F.R. (Code of Federal Regulations) of the Department of Health and Human Services is an example. 21 C.F.R. §1020.32e specifies what is known as the maximum allowed input exposure rate, thus the entrance skin dose rate in mGy/s on the side of a patient facing towards the radiator.

The dose rate radiated by an x-ray source onto a given monitoring surface decreases quadratically with the distance of the monitoring surface from the x-ray source. A minimum distance that must be maintained between a biological tissue and the focus of an x-ray source or the x-ray tube in order to not exceed the prescribed limit dose rate (thus the entrance exposure rate) is calculated from the quadratic distance rule and a predetermined maximum value (limit value).

This minimum distance is primarily dependent on the primary dose rate radiated by the x-ray source and thus is dependent on the limit energy of the x-ray radiation as well as on the maximum achievable beam current.

In specific x-ray applications, the distance between the x-ray radiation for us and the patient is always fixed. The x-ray radiation is then set (by the design of the x-ray tube or by the voltage/current generator or by side filters placed in the beam path) such that no patient is irradiated with an unacceptably high dose rate.

The behavior is different in x-ray systems of the type used, for example, in urology. In arrangements known as under-table fluoroscopy workstations, the x-ray radiator is located under a patient table. The patient table is adjustable in terms of height, meaning that the distance between a patient reclining on the table, or the table surface and the x-ray radiator or its focus is variable. Table positions of different heights are desirable so that a urologist working at the table or on the patient located thereon can move the table into an ergonomically-advantageous working position.

For the most part, the patient table can be moved toward the x-ray radiator so far that, upon operation of the x-ray radiator, the patient lying on the table would be irradiated with an unacceptably high dose rate. If the urologist is standing, the table is generally upwardly by a relatively large distance, causing the patient to be positioned outside of the critical dose rate. An x-ray fluoroscopy of the patient is then possible without danger. For longer endo-urological procedures under x-ray monitoring, however, the urologist usually prefers to be seated, so the patient is moved downwardly, thus very close to the x-ray radiator. The minimum distance may then no longer be adhered to, which (given an activated x-ray source) would lead to an unacceptably high entrance dose rate at the patient.

Various technical possibilities are known in order to always prevent exposure of the patient with a dose rate that is too high. In the designer installation of an x-ray source, fixed primary aluminum filters can be installed in the x-ray radiator in the beam path of the x-ray system between the x-ray source and the patient in order to decrease the maximal primary dose rate that can be emitted by the x-ray source and that can actually strike the patient. The safety distance between the x-ray source and the patient, thus the minimum allowable distance, is thus smaller than without a primary aluminum filter, so that (for example) a urological work table can be lowered further. The radiation, however, is hardened by the primary aluminum filter, causing the image noise in the x-ray image to increase in a disruptive manner, and in fact at distances between the patient and the x-ray source that would be non-critical given unattenuated x-ray radiation (without an aluminum filter). Metal filters (also made from copper) filter the soft radiation portion from the x-ray radiation; so the generated image is thus also higher-contrast, but the image brightness remains.

Furthermore, it is known to mechanically limit the movement path of the patient table in a fixed manner such that thus cannot be moved closer to the x-ray source than is prescribed by the safety interval. This limits the ergonomics of the arrangement since the table is precluded from being lowered when the urologist would like to execute a procedure without x-ray exposure.

It is also known to deactivate the x-ray source or to block triggering thereof if and when the safety interval is not adhered to. In such a table position, however, x-ray fluoroscopy of the patient is no longer possible at all. In such a situation, the doctor must refrain from moving the x-ray table into a position that is ergonomically advantageous for him or her, or must move it upwardly from a convenient working position in order to obtain a fluoroscopy of the patient.

Furthermore, it is known to permanently operate the x-ray radiator below its maximum dose rate, thus with a lower product made up of beam current and acceleration energy than the x-ray source could actually maximally emit. This likewise leads to a permanent decrease of the maximum safety distance. As in the case of a permanently-installed filter, however, the image quality of the x-ray system is generally degraded since the x-ray source is never operated at its optimal operating point. This also applies for table positions that are actually situated above the safety distance and would otherwise allow a higher image quality. The decrease of the generator power leads to a decrease of the number of generated x-ray quanta and an increase of the quantum noise. The x-ray image is coarser, appears noisy and is no longer regarded as being acceptable.

All known solutions are thus compromises between the x-ray contrast or the x-ray image quality and the ergonomics of the overall arrangement.

SUMMARY OF THE INVENTION

An object of the present invention is to provide a method and a corresponding x-ray apparatus for fluoroscopy of a patient who can be placed at a variable distance relative to an x-ray source wherein the aforementioned problems are avoided or made less severe.

This object is achieved in accordance with the invention by method for fluoroscopy of a patient who can be placed at a variable distance relative to an x-ray source, wherein the dose rate emitted by the x-ray source is reduced given a reduction of the distance and/or increased given an increase of the distance.

The dose rate that can be emitted by the x-ray source thus is no longer the same for all distances between the patient and the x-ray source, but rather is variable. If the patient is farther removed from the x-ray source, the x-ray source thus can be operated with a higher (for example the maximum or system-optimal) dose rate, which leads to high-quality x-ray imaging. Moving the patient closer to the x-ray source is possible until a minimum distance allowable for the currently-used dose rate is achieved. Upon reaching the minimum distance or beforehand, the dose rate emitted by the x-ray source is inventively reduced, and thus there is now a new maximum distance between the patient and the x-ray source. The emitted dose rate is thus always dimensioned such that the minimum distance resulting therefrom is smaller than or equal to the actual distance of the patient from the x-ray source. The patient may then be moved a bit closer to the x-ray source. Upon the patient being moved away from the x-ray source, the dose rate of the x-ray source can be increased again until the minimum distance resulting therefrom is smaller than or equal to the actual distance of the patient from the x-ray source.

This method therefore ensures that the patient is never exposed with a dose rate that is too high. The x-ray imaging can also be continued at distances between the patient and the x-ray source that lie below the safe distance for the maximum output capacity of the x-ray source, without exceeding the limit dose rate, i.e., the maximum allowed dose rate that strikes the patient. Although the image quality is then possibly limited, imaging still occurs without having to move the patient again away from the x-ray source and position that is ergonomic for the doctor can be achieved.

The variation of the dose rate can be implemented before or during a treatment on the patient. The doctor thus can select arbitrary distances that are optimal for him or her between the x-ray source and the patient. The possible degradation of the image quality of the x-ray images that is involved with a reduction of the dose rate is, under the circumstances, less important for the doctor than the achieved better ergonomics. By the inventive method, an optimal compromise of image quality and patient position relative to the x-ray source can always be found.

The variation of dose rate that can be emitted by the x-ray source can be undertaken in steps. For example, the dose rate arriving at the patient could be held constant when the dose rate that can be emitted by the x-ray source is varied approximately proportional to the distance between the patient and the x-ray source. The patient thus would always be exposed with the maximum allowable dose rate, which always leads to the best possible image quality of the x-ray images at a given patient distance from the x-ray source.

Alternatively, the dose rate can be varied in steps given specific interval limits of the distance between the patient and the x-ray source. For example, an interval limit exists that is associated with the maximal emittable power of the x-ray source. For intervals (spacings) above this interval limit, the patient is in no way irradiated with a dose rate that is too high, even when the x-ray source radiates with its system-dependent maximum dose rate. Moreover, further interval limits can be predetermined that are respectively associated other reduced output capacities of the x-ray source. The output power radiated by the source is then constant between two interval limits such that, for example, the remaining components of the imaging system can likewise be adjusted in steps to the respective source characteristic. Complicated, continuous updating tracking of the component properties is thus avoided.

The variation of the dose rate upon the distance (the current distance) approaching an interval limit can be terminated beforehand. A person implementing the method thus has discretion to leave a patient (for example) slightly above or slightly below a specific interval limit in order to avoid a reduction of the dose rate emitted by the x-ray source, so as to not impair the image quality of x-ray exposures. A possible decisive advantage in image quality can thus be achieved through a slight loss in ergonomic comfort.

The dose rate can be automatically varied. The implementing person thus does not have to attend to the adherence to safety intervals or the like since, for example, the dose rate is automatically adapted given free selection of the patient distance from the x-ray radiator or a suitable patient distance is set given prior selection of a specific image quality. For example, in a critical phase of an operation the doctor can thus automatically attain an x-ray image with improved image quality simply by raising the treatment table.

Various alternatives alone or in combination are possible in order to reduce the dose rate that the patient experiences from the x-ray source. The location of the dose reduction is unimportant. This can already ensue in the x-ray source itself as an upstream measure at the x-ray source, or proximal to the patient. Only the arrangement of the attenuation in the beam path between source and patient is important.

To reduce the dose rate, a filter can be brought between the x-ray source and the patient. This is brought into the beam path of the x-ray radiation between the x-ray source and the patient or removed again from this beam path dependent on the interval. In contrast to known permanently-installed filters, this filter is inventively only pivoted into the beam dependent on the interval, thus is present between x-ray source and patient only when the dose rate at the patient would otherwise be too high. Given increase of the distance between patient and x-ray source, the filter can be pivoted out of the beam again, so the full dose rate and full image quality of the x-ray imaging is produced again. A metal filter (for example a copper filter) can be used as such a filter. Such copper filters are already present in many x-ray sources, but must be manually pivoted by the doctor before the beginning of the treatment or the imaging. Interaction with the minimum safe distance is not provided.

The method can be executed particularly simply when the filter is brought between the x-ray source and the patient in a motorized manner. The entire method thus can be automated with no personnel for manual pivoting being necessary.

If the maximum dose rate of the x-ray source is predetermined by a power-limited current-voltage characteristic curve (the term "curve" encompassing a linear relationship), a characteristic curve with lower maximum dose rate thus can be used to reduce the dose rate. The output dose rate is likewise reduced by the use of different characteristic curve in the x-ray source or the associated activation, which likewise allows an approach of the patient towards the x-ray source without exceeding the maximum entrance dose rate. Such a decrease of the dose rate is achieved purely electronically, meaning that no moving parts must be pivoted into the x-ray beam path as above. The dose rate reduction by selection of a different characteristic curve can be used alternatively or additionally with pivoting the aforementioned radiation or dose filter.

As alternative characteristic curves to the characteristic curve of maximum dose rate, characteristic curves with limited beam currents and voltages varying mutually therewith can be used. The beam characteristic of the beam source thus is retained; only the output power is reduced. Subsequent image processing or other measures do not have to be adapted to a new characteristic curve of the x-ray source. Moreover, the control mode of the dose rate regulation is not significantly changed.

As an alternative or in addition to the aforementioned alternatives, the x-ray source can be deactivated to reduce the dose rate. The x-ray irradiation onto the patient can be completely stopped in the event that, given the current distance between patient and x-ray source), the dose rate emitted by the x-ray source cannot otherwise be decreased sufficiently so that the patient is irradiated without danger. X-ray imaging is, however, then no longer possible.

The dose rate can be varied (decreased or raised) in a multi-step adjustment procedure. For example, given approach of the patient toward the x-ray source the dose rate is hereby successively decreased in a number of adjustment steps such that the critical minimum interval of patient and x-ray source always drops with the approach of the patient toward the source, such that the patient never reaches this critical minimum distance. Given distancing of the patient from the source, the dose rate of the x-ray source can be successively increased again as soon as the patient has passed the safety interval of the next-highest possible dose rate.

The aforementioned object of the invention also is achieved by an x-ray apparatus for fluoroscopy of a patient who can be placed at a variable distance relative to an x-ray source, with a device for automatically varying the dose rate that can be emitted by the x-ray source, dependent on the distance.

The inventive x-ray apparatus explained above is operable in accordance with all of the embodiments of the inventive method.

The aforementioned filters that can be pivoted into the x-ray path between x-ray source and patient to reduce the dose rate (for example metal filters such as copper filters) thus can be used in the inventive apparatus as the device for variation of the dose rate dependent on the distance.

Alternatively or additionally, the device can be a device for selection of various characteristic curves respectively having various maximum dose rates, when the maximum dose rate of the x-ray source is predetermined by a power-limited current-voltage characteristic curve. This can ensue, for example, by a suitably-adapted activation of the x-ray source or x-ray tube, by a generator equipped with such a set of characteristic curves.

The device can also be a device for blocking activation or triggering of the x-ray source. If and when maximum distance is not adhered to, the x-ray source can then no longer be activated or an x-ray exposure shot can no longer be initiated. This can be realized, for example, by a simple mechanical switch.

Naturally, if the method is automated the x-ray apparatus must possess components such as a distance sensor for the distance or the interval of the patient from the x-ray source, a corresponding workflow controller (for example by hardware or software in the x-ray system) and further self-evident system components.

DESCRIPTION OF THE PREFERRED EMBODIMENTS

Figure 1:
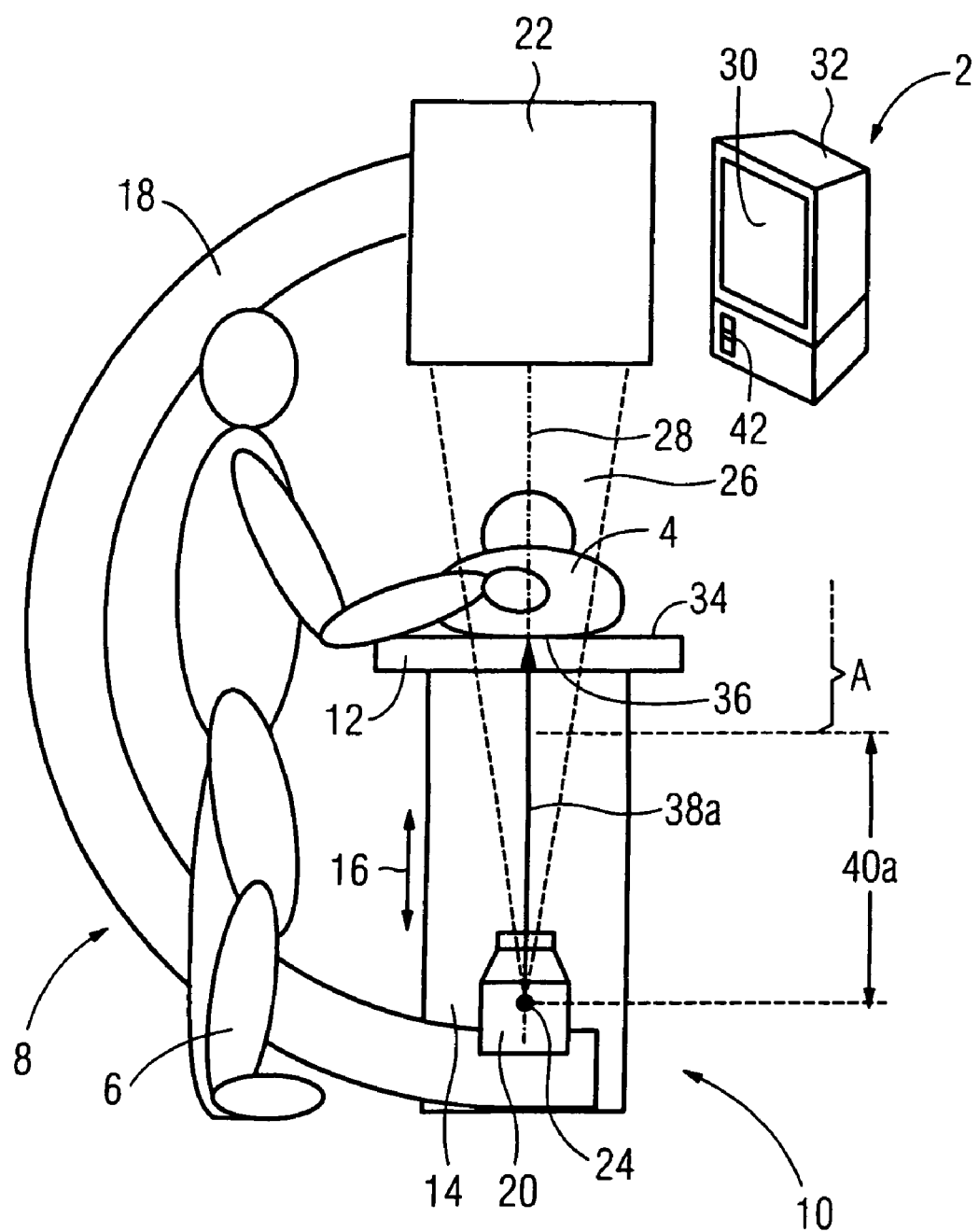
FIG. 1 shows a urological under-table fluoroscopy workstation with patient and standing urologist.

FIG. 1 shows a urological workstation 2 with a patient 4 and a doctor 6. The workstation 2 has an x-ray C-arm unit 8 and a patient table 10 with a table plate 12 on which the patient 4 lies. The table plate 12 is supported on a base 14 such that it can be adjusted in terms of height in the direction of the double arrow 16. The height adjustment ensues by actuation of a control (operating) lever 42 in a manner that is not necessary to explain in detail.

The x-ray C-arm unit 8 has a C-shaped supporting arm 18 at the ends of which an x-ray source 20 and an x-ray image intensifier 22 are mounted, respectively. In the x-ray source 20 (more precisely, the x-ray tube contained therein and not shown), x-ray radiation 26 (represented in FIG. 1 by a beam cone) is emitted from the focus 24 along a central ray 28 toward the x-ray image intensifier 22. The x-ray radiation 26 penetrates the patient 4 in order to generate an x-ray image 30 of the inside of the body in a known manner, this x-ray image 30 is displayed to the doctor 6 on a monitor 32. Since the x-ray source 20 is arranged below the table plate 12, in the workstation 2 is known as an under-table arrangement, but the invention can naturally be transferred to all other arrangements (for example above-table).

Since the patient 4 lies on the table plate 12, the top side 34 of the table plate 12 is the lowest possible position at which the patient 4, or his or her body parts (at the back 36) rests. This means that the smallest possible distance between the focus 24 and the body of the patient 4 is the distance between the focus 24 and the top side 34 of the table plate 12. In FIG. 1, this distance is indicated as a double arrow representing the actual current distance 38a between the patient 4 and the focus 24. Given a height adjustment of the patient table 10 by adjusting the height of the table plate 12, this current distance 38a changes. For example, upon lowering of the table plate 12 in the direction of the x-ray source 20 the distance becomes smaller.

Dependent on its design or due to its activation, each x-ray source 20 has a maximum output dose rate $P_{max}$ of x-ray radiation 26 which, in the extreme case, is completely incident on the body of the patient 4. Given a designation or fixed output power of the x-ray source 20, the dose rate (known as the entrance skin dose rate Pin) exposing the patient 4 at the side of the entrance of the radiation into the body of the patient 4 then depends on the distance 38a and $P_{max}$ according to a quadratic distance rule. For example, legal prescribed limit values $P_{limit}$ which cannot be exceeded exists for this entrance skin dose Pin reaching the patient. A minimum distance 40a of the patient 4 from the focus 24 thus can be calculated from the beam geometry of the x-ray radiation 26 and the distance 38a. At least this minimum distance 40a must be adhered to so that the patient 4 is exposed only with the maximum allowable entrance skin dose $P_{in} \leq P_{limit}$.

As long as the top side 34 of the table plate 12 in FIG. 1 is located in the interval range A, meaning that the current distance 38a is greater than the minimum distance 40a (which applies in FIG. 1), even given a maximal output power $P_{max}$ of the x-ray source 20 it is always ensured that the patient 4 is not exposed with an unacceptably-high entrance skin dose $P_{in} > P_{limit}$ of the x-ray radiation 26. The x-ray source is therefore operated with the output power $P_A = P_{max}$ in the entire interval range A.

In the entire interval range A, the doctor can therefore adjust (displace) the table plate 12 via the control lever 42 until a treatment position or working position that is ergonomically convenient for the doctor has been found in order to implement a task on the patient 4. For example, in FIG. 1 the doctor 6 (a urologist) implements auxiliary measures on the patient 4 under x-ray monitoring (i.e. given activated x-ray radiation 26) while standing.

Figure 2:
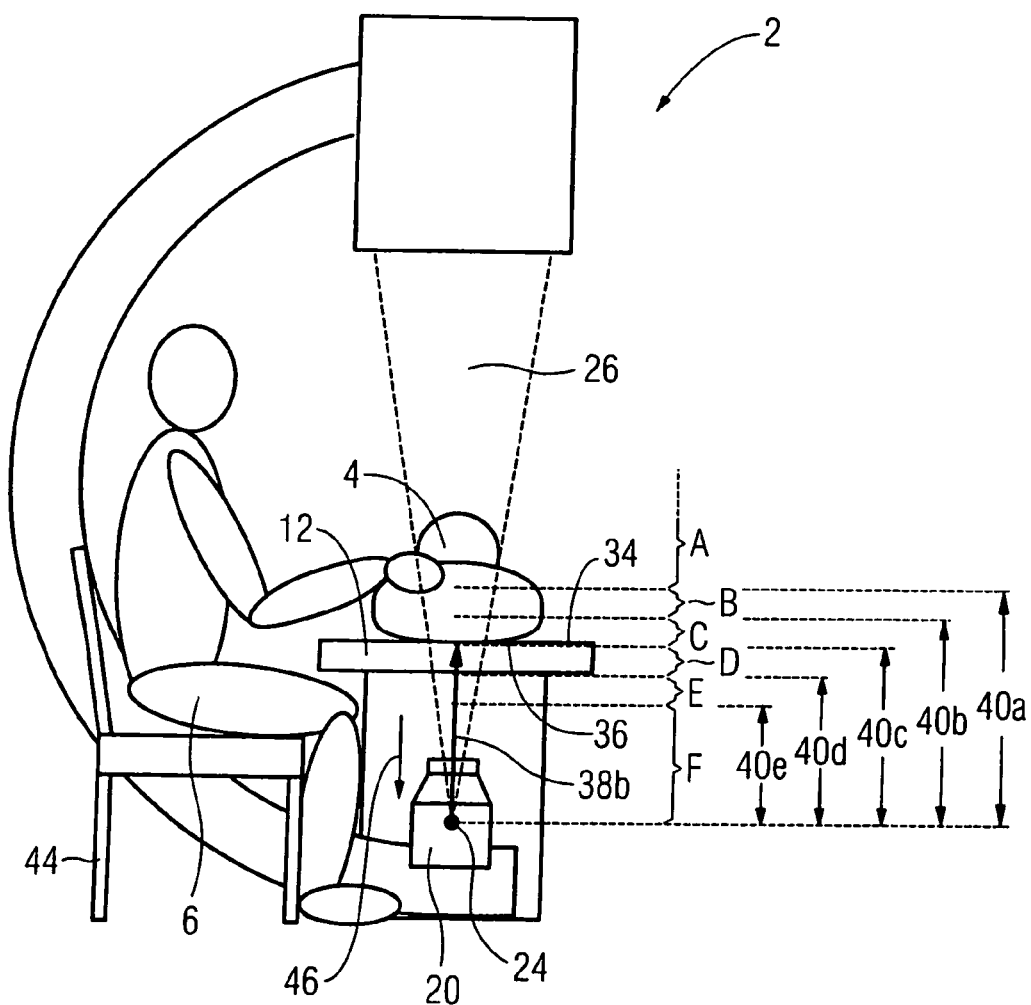
FIG. 2 shows the workstation of FIG. 1 with a seated urologist and lowered patient.

After the implementation of the auxiliary measures, the treatment of the patient 4 begins without an interruption. FIG. 2 therefore shows the workstation 2 of FIG. 1 at a later point in time, namely when the doctor 6 implements an endo-urological procedure on the patient 4 under x-ray monitoring. In order to satisfy the ergonomic requirements of the doctor 6 during this treatment, the doctor is seated on a stool 44. The position of the patient 4 shown in FIG. 1 would be unsuitable for this. In order to move the patient 4 further into a working position that is ergonomically advantageous for the doctor 6, the doctor 6 lowers the table plate 12 (using the control lever 42) together with the patient 4 in the direction of the x-ray source 20, thus in the direction of the arrow 46.

The top side 34 of the table plate 12 and thus the back 36 of the patient 4 now exhibits a changed (namely smaller) current distance 38b from the focus 24 relative to FIG. 1. If the x-ray source 20 were to again radiate with the maximal dose rate PA explained in FIG. 1, the back 36 of the patient 4 would be exposed with an unacceptably high entrance skin rate $P_{in}>P_{limit}$ of x-ray radiation 26, which represents an unallowable situation. For this reason, the output dose rate of the x-ray source 20 in FIG. 2 is reduced to a value $P_C<P_A$. A minimum distance 40c that is reduced relative to the minimum distance 40a thus results for the output power $P_C$ of the x-ray source 20 selected in FIG. 2. Since the current distance 38b of the patient 4 from the focus 24 is greater than the minimum distance 40c, the patient furthermore experiences only an entrance skin dose rate $P_{in}<P_{limit}$ via the x-ray radiation 26 which is smaller than the maximum allowed entrance skin dose.

Furthermore, from FIG. 2 it is apparent that if one starts from an initial situation according to FIG. 1, upon lowering in the direction of the arrow 46 the top side 34 of the table plate 12 passes through the interval ranges A to F. In each of these interval ranges, the x-ray source 20 is operated with a continuously smaller power $P_F<P_E<P_D<P_C<P_B<P_A$. Toward the focus 24, the corresponding interval ranges A-E are therefore respectively limited by the minimum distances 40a-40e calculated from the respective power.

Upon reaching each minimum distance 40a-40e, the power of the x-ray source 20 is reduced successively and in steps such that the effective minimum distance is reduced to the next following minimum distance. Given lowering of the table plate 12 from the position shown in FIG. 1 (there the minimum distance 40a applies), the output power $P_A$ is thus initially reduced to the output power $P_B$ upon reaching the minimum distance 40a, and the minimum distance 40b applies. A further decrease of the table plate 12 through the range B ultimately leads to this reaching the distance limit 40b, such that the output power of the x-ray source 20 is in turn decreased by a specific value to the output power PC, and the effective minimum distance is reduced to the distance 40c.

This procedure ends when the minimum distance 40e is reached after passing through the interval range E. No further reduction of the output power of the x-ray source 20 below the minimum distance 40e is possible or reasonable since an effective x-ray imaging in the workstation 2 is then no longer possible. In the interval range F, the x-ray source 20 is therefore completely deactivated, or an activation of the x-ray source 20 for an exposure shot is prevented.

Upon raising the patient table 10 counter to the direction of the arrow 46, the corresponding interval ranges F-A are traversed in the reverse order, and the output power of the x-ray source is successively increased by the aforementioned power steps. If the top side 34 of the table plate 12 reaches the minimum distance 40a and the table plate 12 henceforth moves into the interval range A, the x-ray source returns to its maximal output power PA.

Figure 3:
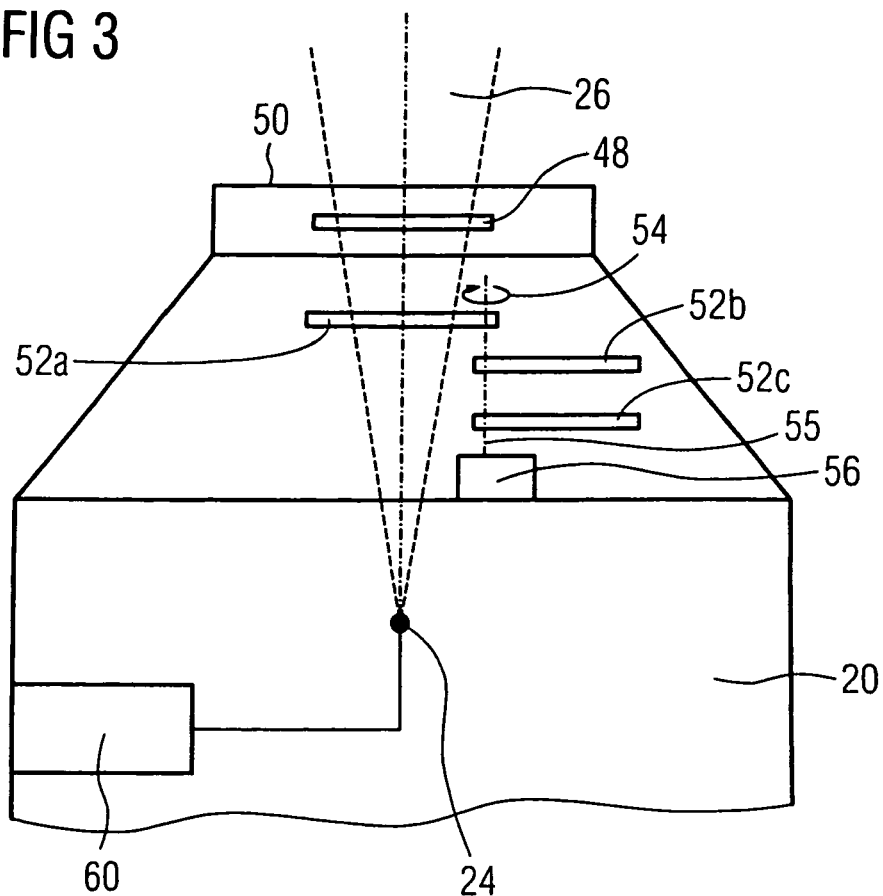
FIG. 3 shows the x-ray source of FIG. 1 in an enlarged representation.
Figure 4:
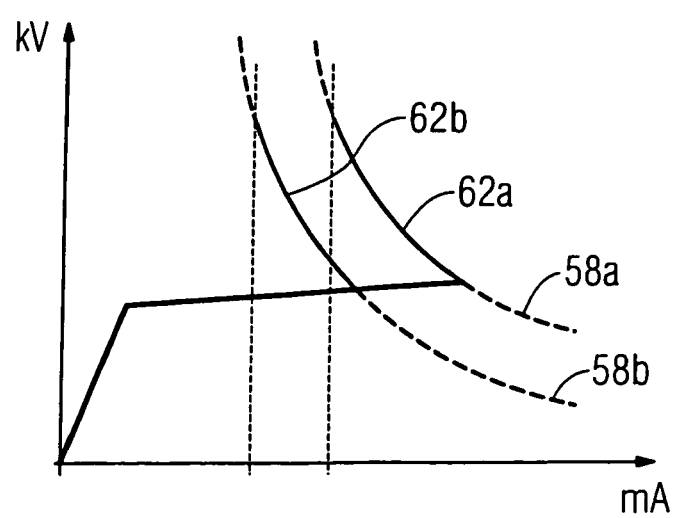
FIG. 4 shows a characteristic curve set associated with the x-ray source of FIG. 1.

For the step-by-step attenuation of the output power of the x-ray source, what is known as an escalation method is used whose execution is explained using FIGS. 3 and 4.

FIG. 3 shows a partial view of the x-ray source 20 of FIG. 1 and FIG. 2, with the focus 24 of the x-ray tube (not shown) being indicated as the source of the x-ray radiation 26. For global power limitation of the x-ray radiation 26 that can be emitted from the x-ray source 20, primarily aluminum filters 48 are permanently mounted in the x-ray source 20 (for example screwed into the x-ray source 20) in the design or installation of the workstation 2. The aluminum filters 48 limit the maximum internal x-ray power $P_{intern}>P_{max}$ of the x-ray tube that can be emitted at the focus 24, such that only a maximal power $P_{max}$ can be emitted at the exit aperture 50 of the x-ray source 20.

Copper filters 52a-52c are additionally provided in the x-ray source 20. Each of the copper filters 52a-52c can be pivoted into and out of the beam path of the x-ray radiation 26 in the direction of the arrow 54, independently of one another. For this purpose, they are supported on axles 55 (not shown in detail) that are driven by a motor 56. In contrast to FIG. 1, in FIG. 3 the first copper filter 52a is already pivoted into the beam path of the x-ray radiation 26, causing the exit dose rate of the x-ray source 20 to be reduced from the value PA to the value PB. The configuration of pivoted-in copper filter 52a and pivoted-out copper filters 52b and 52c shown in FIG. 3 therefore applies for the interval range B. Although the rough contrast in the x-ray image 30 hereby decreases, given a continued imaging further work can still be done below the previous minimum distance 40a.

To achieve a further attenuation of the output power of the x-ray source 20 to the value PC, a further measure is used, which is explained using FIG. 4. The characteristic curve set of the x-ray source 20 or of the associated generator 60 (i.e. the generator 60 driving the x-ray tube) is shown in FIG. 4. The beam current is plotted on the abscissa and the generator voltage is plotted on the ordinate for two different characteristic curves 62a and 62b in FIG. 4. The maximum output dose rate $P_{max}$ that can be emitted by the x-ray source 20 is predetermined by the power hyperbola 58 (taking into account the permanently-installed aluminum filters 48) that is approached by the characteristic curve 62a.

To decrease the internal dose rate $P_{intern}$ emitted at the focus 24 by the x-ray tube (not shown), the x-ray source 20 is switched to a second power hyperbola 58b by the system controller or the generator 60 in the interval range C, D and E (as, for example, in FIG. 2). It is thus operated with a different characteristic curve 62b that is characterized by a maximum output power $P_{intern}$ of the x-ray tube that is limited relative to the power hyperbola 58a. An exposure correction (not shown) in the x-ray system compensates (within certain limits) the lower receiver dose; the image 30 behaves noisier, but it can still be used.

The dose rate generated at the focus 24 and already reduced according to the characteristic curve 58b is thus reduced to the maximum value $P_C$ at the exit aperture 50 by the copper filter 52a that is pivoted-in in the interval ranges B, C, D and E.

For further reduction of the output power of the x-ray source 26, the second copper filter 52b is additionally pivoted into the x-ray radiation 26 in the interval range D and the third copper filter 52c is additionally pivoted into the x-ray radiation 26 in the interval range E. As already noted, the table plate 12 can be moved up to the minimum distance 40e relative to the focus 24 with such reduced output power PE given pivoted-in copper filters 52a-52c and reduced characteristic curve 62b.

Upon the minimum distance 40e not being satisfied, the generator 60 deactivates the x-ray tube so that no further x-ray radiation 26 is generated at the focus 4. The output power PF is thus zero. The generator 60 acts as an activation block of the x-ray source 20, so to speak.

The characteristic curves 62a and 62b oriented on the power hyperbola 58a and 58b are correlated such that the radiation characteristic or the operating behavior of the x-ray source 20 does not change when the output power is reduced according to power hyperbola 58b, which leads to the x-ray behavior of the workstation 2 being identical up to the limit power. Only the image quality changes given each transition between two interval ranges.

Both the pivoting-in and pivoting-out of the copper filters 52a-52c and the switch between the characteristic curves 62a and 62b ensue wholly automatically depending on the determined distance 38a, 38b, such that the doctor 6 merely needs to concentrate on the lowering or raising of the table plate 12 with the control lever 42. The doctor 6 is informed on the monitor 32 of the current table position or the attainment of or the distance from various minimum distances 40a-40e. For example, by raising the table 12 by a few cm the doctor 6 can decide to have available x-ray radiation 26 of a higher dose rate when a limit between two interval ranges is exceeded. Given a minimal loss of comfort, this means that an x-ray image 30 of improved image quality is acquired.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for obtaining a fluoroscopic image of a subject using x-rays emitted from an x-ray source at a dose rate, said subject being placeable at a variable distance relative to said x-ray source, comprising the steps of:
   reducing said dose rate upon a reduction of said variable distance;
   increasing said dose rate upon an increase of said variable distance;
   establishing successive predetermined distance limits between said x-ray source and the patient;
   respectively increasing and decreasing said dose rate in steps with respect to said distance limits with step changes in said dose rate respectively occurring at said distance limits; and
   as said variable distance is increased or decreased, generating a humanly perceptible indicator as the respective distance limits are approached before changing the dose rate.

2. A method as claimed in claim 1 comprising automatically reducing said dose rate upon said reduction of said variable distance and automatically increasing said dose rate upon said increase of said variable distance.

3. A method as claimed in claim 1 comprising reducing said dose rate by placing a filter between said x-ray source and said patient, and increasing said dose rate by removing said filter.

4. A method as claimed in claim 3 comprising employing a copper filter as said filter.

5. A method as claimed in claim 3 comprising bringing said filter between said x-ray source and said patient, and removing said filter, by motorized control of said filter.

6. A method as claimed in claim 1 wherein a maximum dose rate of said x-ray source is predetermined by a power-limited, current-voltage characteristic curve at which said x-ray source is operated, and comprising:
   storing a set of characteristic curves respectively for dose rates below said maximum dose rate; and
   reducing said dose rate upon said reduction of said variable distance by selecting one of said characteristic curves and operating said x-ray source with the selected characteristic curve.

7. A method as claimed in claim 6 wherein said x-ray source has a beam current during operation thereof, and comprising storing respective characteristic curves, as said set of characteristic curves, having respectively different limited beam currents.

8. A method as claimed in claim 1 comprising reducing said dose rate upon said reduction of said variable distance by deactivating said x-ray source.

9. A method as claimed in claim 1 comprising decreasing said dose rate in multiple steps during said reduction of said variable distance and increasing said dose rate in multiple steps during said increase of said variable distance.

10. An x-ray fluoroscopy apparatus for obtaining a fluoroscopic image of a subject, comprising:
    an x-ray source that emits x-ray radiation at a dose rate;
    a patient table configured to receive a patient thereon, said patient table being adjustable to selectively place the patient at a variable distance relative to said x-ray source, said variable distance comprising a plurality of successive predetermined distance limits;
    an imaging system that produces a fluoroscopic image of the patient from x-rays emitted by said x-ray source and attenuated by the patient;
    a controller that operates said x-ray source to set the dose rate thereof, said controller automatically varying said dose rate dependent on said variable distance to reduce said dose rate upon reduction of said variable distance and to increase said dose rate upon an increase of said variable distance, said controller respectively increasing and decreasing said dose rate in steps with respect to said distance limits with step changes in said dose rate respectively occurring at said distance limits; and
    an indicator device that provides a humanly perceptible indicator upon each of said distance limits being approached before said controller changes said dose rate.

11. An x-ray apparatus as claimed in claim 10 comprising a filter device that automatically moves a filter into and out of the x-rays emitted by said x-ray source between said x-ray source and the patient, dependent on said variable distance.

12. An x-ray apparatus as claimed in claim 11 wherein said filter is a copper filter.

13. An x-ray apparatus as claimed in claim 10 wherein said x-ray source has a maximum dose rate that is predetermined by a power-limited, current-voltage characteristic curve with which said x-ray source is operated, and wherein said controller has a set of different characteristic curves stored therein with respectively lower dose rates than said maximum dose rate, and wherein said controller automatically selects one of said stored characteristic curves for operating said x-ray source dependent on said variable distance.

14. An x-ray apparatus as claimed in claim 10 wherein said controller also activates and deactivates said x-ray source dependent on said variable distance.

* * * * *